United States Patent [19]
Case

[11] Patent Number: 5,183,326
[45] Date of Patent: Feb. 2, 1993

[54] UNDERWATER FLASHLIGHT HOLDER

[75] Inventor: Richard N. Case, Boulder, Colo.

[73] Assignee: RCP Enterprises, Inc., Boulder, Colo.

[21] Appl. No.: 842,016

[22] Filed: Feb. 25, 1992

[51] Int. Cl.⁵ .................................................. F21L 7/00
[52] U.S. Cl. .................................. 362/191; 362/105; 362/208; 362/396; 2/209.2; 224/181
[58] Field of Search ............... 362/106, 105, 103, 190, 362/191, 208, 253, 396, 385; 2/209.2; 224/181

[56] References Cited

U.S. PATENT DOCUMENTS

| | | | |
|---|---|---|---|
| 4,429,350 | 1/1984 | Guthrie | 362/190 X |
| 4,638,410 | 1/1987 | Barker | 362/105 |
| 4,734,834 | 3/1988 | Petzl et al. | 362/105 X |
| 4,817,212 | 4/1989 | Benoit | 362/106 X |
| 4,998,187 | 3/1991 | Herrick | 362/105 X |

Primary Examiner—Stephan F. Husar
Attorney, Agent, or Firm—Donald W. Margolis; Edwin H. Crabtree

[57] ABSTRACT

Apparatus for holding a flashlight or other small object adjacent to the side of the head of an underwater diver, thereby freeing the hands of the diver for other purposes, while still providing underwater lighting or other equipment. It is designed for releasable connection to head gear worn by underwater divers, and includes an element for providing support to a flashlight. The support preferably has a specific gravity of less than about one, thereby providing floatation to the apparatus and to any article which is carried by the apparatus, as well as support and orientation to a flashlight or other equipment which is carried by the apparatus. The support is connected to the head gear of a diver and to a flashlight by one or more strap which releasably engages and secures the flashlight to the support, and which strap also releasably engages and secures the support and the flashlight which it carries to the diver. The apparatus also includes a structure for orienting the light beam of a lit flashlight inwardly in the direction of the line of sight and close range visual focus of a diver when underwater. The flashlight is secured to the support at a distance away from the head of a diver in order to keep the beam of a lit flashlight from being deflected by any head gear worn by the diver.

20 Claims, 6 Drawing Sheets

UNDERWATER FLASHLIGHT HOLDER

BACKGROUND OF THE INVENTION (a) Field of the Invention

This invention relates to a flashlight holder for carrying a flashlight adjacent to the side of a head of an underwater diver, and more particularly, but not by way of limitation, to an apparatus for holding a flashlight underwater and directing the beam of light from the flashlight toward the line of sight of an underwater diver.

(b) Description of the Prior Art

Heretofore there have been a variety of different types of underwater illumination devices for providing light underwater for divers and swimmers. These devices are described in U.S. Pat. No. 4,429,350 to Guthrie; U.S. Pat. No. 4,638,410 to Barket; U.S. Pat. No. 4,734,834 to Petzl et al; and U.S. Pat. No. 4,817,212 to Benoit;

Also there are a variety of different types of flashlight headbands and retainers described in the following patents: U.S. Pat. No. 5,053,932 to the subject inventor, Richard N. Case; U.S. Pat. No. 5,034,862 to Liston; U.S. Pat. No. 4,970,631 Marshall; U.S. Pat. No. 4,887,194 to Fields; U.S. Pat. No. 4,797,793 to Fields; U.S. Pat. No. 4,729,499 to Martin; U.S. Pat. No. 4,718,126 to Slay; U.S. Pat. No. 4,360,930 to Blanchard; and U.S. Pat. No. 3,249,271 to Allbritton.

Also of specific interest in U.S. Pat. No. 4,870,550 to Uke, which discloses a specific form of waterproof flashlight which is designed to receive at least two parallel adjacent rows of batteries, and including a connecting device and a watertight sealing device. The product of this patent is commercially available from Underwater Kinetics of San Marcos, Calif., which in its operational form, including batteries and a bulb has been found to have a specific gravity of greater than one, and to sink when released in water. In one form, the Mini Q40, straps for connecting the flashlight to the strap of a dive mask are provided, but in this embodiment the light of the flashlight is immediately adjacent to the head of the diver, includes no support element, and has a specific gravity of greater than one, and will sink when released in water.

None of the above mentioned prior art patents provide a light weight, inexpensive, streamlined apparatus for holding a flashlight or other small object adjacent to the side of the head of an underwater diver, thereby freeing the hands of the diver for other purposes, while still providing underwater lighting or other equipment. None of the above mentioned prior art patents provide such an apparatus which is designed for releasable connection to head gear worn by underwater divers, and which includes an element for providing combined support and orientation to a flashlight, including a combined support and orientation element which has a specific gravity of less than one, thereby providing floatation to the apparatus and to any article which is carried by the apparatus, as well as support and orientation to a flashlight or other equipment which is carried by the apparatus. None of the above mentioned prior art patents provide such an apparatus which includes a system for releasably connecting it to the head gear of a diver and to a flashlight, or which further includes a structure for orienting the light beam of a lit flashlight inwardly in the direction of the line of sight and close range visual focus of a diver when underwater, yet in which the flashlight is secured to the support at a distance away from the head of a diver in order to keep the beam of the lit flashlight from being deflected by any head gear worn by the diver.

SUMMARY OF THE INVENTION

It is therefore an object of the present invention to provide a light weight, inexpensive, streamlined apparatus for holding a flashlight or other small object adjacent to the side of the head of an underwater diver, thereby freeing the hands of the diver for other purposes, while still conveniently providing underwater lighting or other equipment.

Another object of the present invention is to provide such an apparatus which is designed for releasable connection to head gear worn by an underwater diver, and which includes an element for providing support to a flashlight.

Still another object of the present invention is to provide an apparatus for holding a flashlight underwater in which the combined support and article has a specific gravity of less than one, thereby providing floatation to the apparatus and to the flashlight or any other article which is carried by the apparatus, as well as support to the flashlight or other equipment which is carried by the apparatus.

Still yet another object of the present invention is to provide such an apparatus which includes a system for releasably connecting it to the head gear of a diver and to a flashlight.

Another object of the present invention is to provide such an apparatus which includes a structure for orienting the light beam of a lit flashlight inwardly in the direction of the line of sight and close range visual focus of a diver when underwater.

Yet another object of the present invention is to provide a such an apparatus in which the flashlight is secured to the support at a distance away from the side of the head of a diver in order to keep the beam of a lit flashlight from being deflected by any head gear worn by the diver.

A further object of the present invention is to provide an apparatus for holding a flashlight underwater, which apparatus is inexpensive, simple in design yet rugged in construction, colorful, and made of long lasting, durable material.

The present invention provides an apparatus for holding a flashlight or other small object adjacent to the side of the head of an underwater diver, thereby freeing the hands of the diver for other purposes, while still conveniently providing underwater lighting or other equipment. The apparatus is especially designed for releasable connection to head gear of the type which is normally worn by underwater divers, but may also be connected to other dive equipment, or adjacent to other portions of the body of a diver, other than the head. In preferred embodiments the apparatus includes an element for providing support to a flashlight. The flashlight support element will normally have a fixed three-dimensional shape, most commonly that of a regular hexahedron, such as a box, and therefore include a proximal side adapted to be connected adjacent to the head gear of a diver, and a distal side which is opposed to the proximal side. Where the flashlight support element is box shaped or is some other form of hexahedron, it will also include a top portion, a bottom portion, a front end, and a rear end in addition to a proximal side and a distal side.

In preferred embodiments, the flashlight support means has an overall specific gravity of less than about one, thereby providing floatation to the apparatus and to any article, such as a flashlight, which is carried by the apparatus. The floatation which is thereby provided effectively makes the system "lighter than water," or weightless when submerged in water, thereby avoiding a burden to the diver. In one embodiment, as detailed below, substantially the entire flashlight support element has a specific gravity of less than about one, being made, for example, from solid foam material having a specific gravity of about 0.02, whereby the support and orientation element provides buoyancy to the entire apparatus when underwater, as well as support to any flashlight or other equipment which may be carried by the apparatus.

The support element is connected to the head gear of a diver and to a flashlight or other equipment by connecting elements, for example by one or more strap which releasably engages and secures the equipment to the support element, and which strap is also used to releasably engage and secure the support element, including any flashlight or other apparatus which it carries, to the diver. Such straps would include, for example, at least a first end, a second end, and a body portion intermediate the ends, as well as a mechanism for adjustably and releasably attaching one portion of the strap to another portion of the strap around the support element and any flashlight or other apparatus which it carries.

In use, the straps normally circumscribe the floatation support element, and are adapted to be connected to, for example, the strap of the head gear of a diver in a manner such that the proximal side of the floatation support element is secured adjacent the side of the head gear strap or other equipment of a diver.

In one preferred embodiment a portion of the flashlight strap adjacent to its first end is secured to the top portion of the support, and the second end of the strap is threaded down and around the inside of a portion of the head gear strap, passed around the bottom of the support, then looped around the distal side of the support, where the flashlight or other equipment will be located, and then passed over the top of the support and adjustably secured to the first end of the strap, for example, with a buckle, in a manner such that the body portion of the strap substantially circumscribes the support. A flashlight may be place against the distal end of the support before the strap is wrapped around the support, or the strap may be loosened to allow a flashlight to be placed between the distal end of the support, and the strap. The strap can also be adjusted to tighten it to the gear to which it is attached as well as to tighten the flashlight against the distal side of the floatation support in order to hold the flashlight securely in place. In preferred embodiments, a pair of straps are used. The manner in which the straps connect the apparatus to the gear of the diver leaves the apparatus somewhat swingable at a right angle to the length of the straps. When the apparatus is so secured and worn by a diver, and the diver submerges in water, the floatation support element can swing upwardly to provide buoyancy to the flashlight or any other item carried by the apparatus, thereby providing a weightless or a bouyant system.

In addition, a fabric cover or shell may enclose all or a portion of the floatation support element, and the straps may then be connected to the fabric. Where the fabric is a shell which substantially completely surrounds the floatation support element, it will then preferably have a closable opening for receiving a core therein, and a mechanism for closing the opening and securing the core inside of the fabric shell.

Because of its low specific gravity, should the apparatus unintentionally come free from the diver while underwater, instead of sinking, it will float to the surface of the water where it can be recovered. Also this floatation feature allows the apparatus to be intentionally released to float to the surface and act as a signal or location marker day or night.

It is therefore seen that in preferred embodiments, as further detailed below, the flashlight is secured to the distal side of the floatation support element, at a distance from the head of a diver. The distance which is thereby provided to space the flashlight away from the head of a diver is especially useful when the head gear is in the form of goggles, a face mask or any other gear which has a width greater than the width of the head of the diver, as it keeps the flashlight and the flashlight beam from being deflected or from being blocked by such head gear.

In other embodiments, the flashlight or other equipment may be connected to another portion of the floatation support element, or even extend through the floatation support element. In yet other embodiments, a floatation support element and a flashlight may be a combined unit having a total specific gravity of less than about one.

As detailed below, the floatation support element preferably also includes a structure for orienting the light beam of a lit flashlight inwardly in the direction of the line of sight and close range visual focus of a diver when underwater. The structure for orienting the flashlight may be intergral with the floatation support and orientation element, for example, with the distal side angled inwardly from its rear end toward its front end, so that when the apparatus is secured adjacent to the side of head gear worn by a diver who submerges in water, the flotation support and orientation element will bring the beam of a lit flashlight carried by the apparatus into alignment with the short range line of sight in front of the face of the diver.

As used herein, a "flashlight" shall be understood to be a conventional flashlight which includes batteries and a bulb in a housing, or any other source of illumination, or any other equipment which a diver would wish to carry when underwater without encumbering his or her hands.

The "support", or "floatation and orientation support", may by a solid core or a fluid filled container having the desired specific gravity.

As used herein, "head gear" shall be understood to include underwater goggles, underwater masks, diving helmets, head bands, and where appropriate, other gear worn by a diver, and even the body of the diver.

It is thus seen that present invention provides an apparatus which is useful for holding a flashlight or other small object adjacent to the side of the head of an underwater diver, thereby freeing the hands of the diver for other purposes, while still providing underwater lighting or other equipment.

These and other objects of the present invention will become apparent to those skilled in the art from the following detailed description, showing the contemplated novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which.

DESCRIPTION OF THE PREFERRED EMBODIMENT

Figures 1, 2, 3, 4, 5, 6:
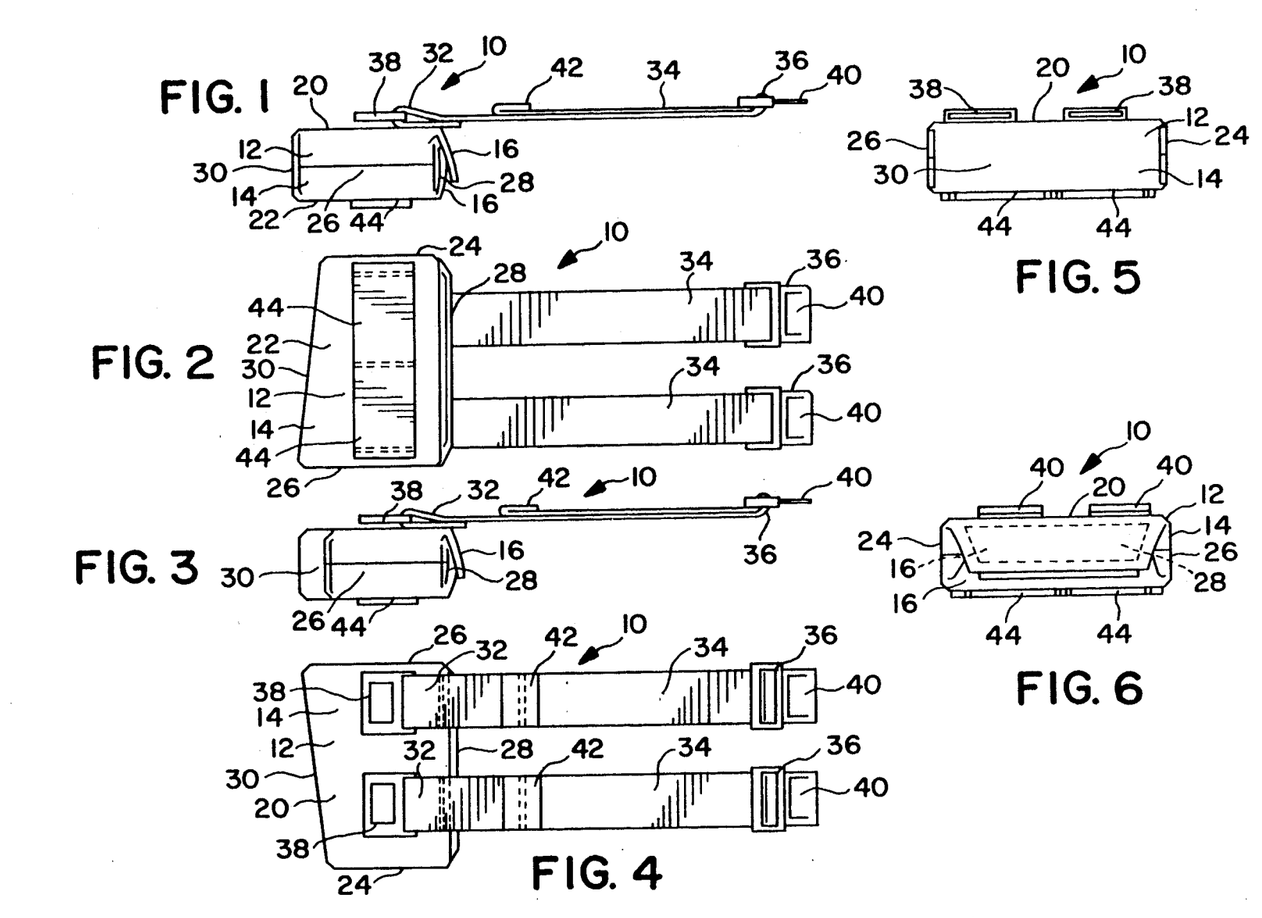
FIGS. 1-6 illustrate, respectively, front side view, a bottom view, a rear side view, a top view, a proximal side view, and a distal view of the subject invention with its straps extended, and with no flashlight attached thereto.
Figure 7:
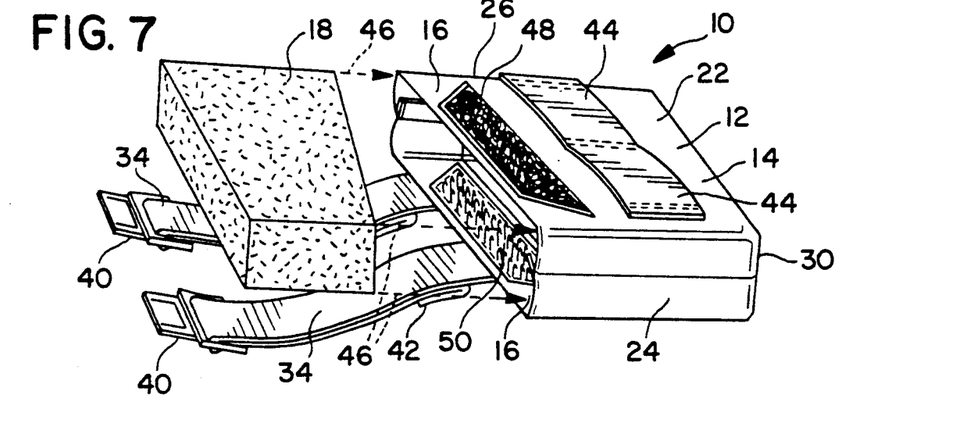
FIG. 7 is an enlarged, exploded bottom perspective view of the apparatus showing an open fabric shell opened for receiving a solid core therein.

Referring to FIGS. 1-6, the subject apparatus for holding a flashlight is shown having a general reference numberal 10. The apparatus 10 is shown in FIGS. 2 and 4 in bottom and top plan views having an angular shaped floatation support member 12. In preferred embodiments floatation support member 12 is composed of a fabric shell 14 made, for example of nylon, and having a pair of folded flaps 16 which are used for opening the shell and receiving a solid core 18 therein, as shown in FIG. 7. The core 18 may be made of polyethylene foam or of a similar product, an preferably has a specific gravity of less than about one, say in the range of about 0.01 and about 0.9.

The floatation support 12 includes a top portion 20, a bottom portion 22, a front end 24, a rear end 26, a proximal side 28 and a distal side 30. Attached to the top portion 20 of the support 12 is a first end 32 of a pair of flaccid straps 34. A low profile connecting system, such as buckle 36 having a female portion 38 and a male portion 40, is provided. The female portion 38 is shown attached to the first end 32 of each strap 34, while the male portion 40 is adjustably mounted on the body portion of each strap 34. While a pair of straps 34 are shown in the drawings, it can be appreciated that a single strap or a plurality of more than two straps can be used equally well for securing a flashlight thereto. In this instance a pair of narrow straps 34 have been found useful in that they can be received through loops (not shown) incorporated into a side of a housing in a modern underwater flashlight.

Referring now to FIG. 2, a bottom view of the apparatus 10 is shown. In this view, a pair of loops 44 are shown connected to the bottom portion 22 of the floatation support 12. The loops 44 are made, for example of strap material similar to straps 34, and are used to receive the male portion 40 of the buckles 36 therethrough and to hold the straps 34 in a stable spaced relationship from each other on the floatation support 12. It should be noted that in this drawing the distal side of the support 12 can be seen angled inwardly from the rear end 26 to the front end 24. This feature is discussed in greater detail with regard to FIGS. 12-13.

In FIGS. 3-4 a front view and a top view of the appartus 10 is shown. The straps 34 are of sufficient length, so that the second end 42 of the straps 34 can be adjusted on the male portion 40 of the buckle 36. This feature allows the circumference of straps 34 to be increased or decreased, depending on the size of the flashlight to be secured to the floatation support 12. FIGS. 5-6 illustrate a view of the distal side 30 of the support 12 and a view of the proximal side 28 of the support 12 with the straps 34 and buckles 36 extending outwardly therefrom.

In FIG. 7 an enlarged, exploded bottom perspective view of the apparatus 10 is shown with the flaps 16 of the fabric shell 14 opened for receiving the core 18 therein as indicated by arrows 46. Once the core 18 is inserted inside the fabric shell 14 of the support 12, the flaps 16 are folded one on top of each other and secured, for example, using a strip of loop material 48 and a strip of hook material 50 of the type known by the trademark of "Velcro". While the material 48 and 50 are shown for securing the flaps 16, it can be appreciated that a number of other types of securing elements could be used equally well for this purpose.

The foam core 18 is sufficiently rigid to resist high pressures associated with scuba diving and other types of diving to depths of 100 feet and greater. Foam having a specific gravity in the range of about 0.01 to about 0.9 has been found to meet the necessary requirements of the subject invention. Because of the buoyancy of the floatation support 12, the apparatus 10, including an attached flashlight, when released will return to the surface of the water where it can be recovered. This feature can act as signal or for marking an underwater location, or merely to avoid the loss of the apparatus and flashlight due to sinking when the apparatus is inadvertently released.

Figure 8:
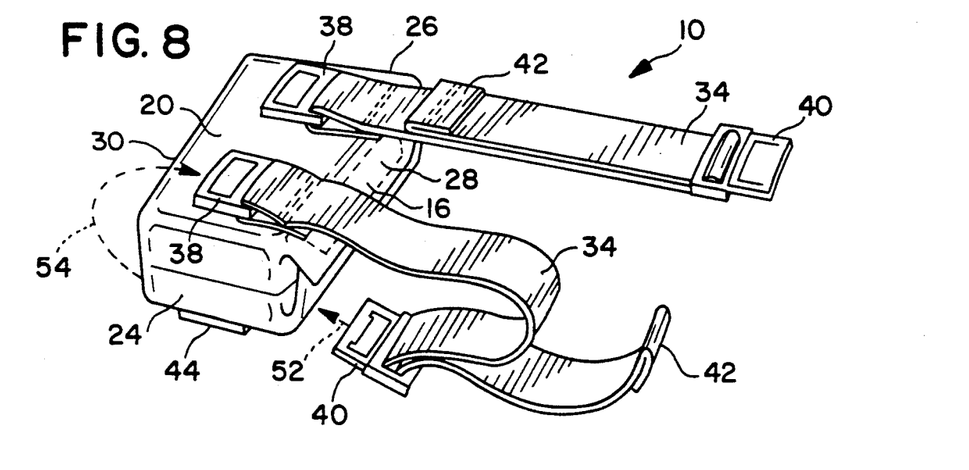
FIGS. 8 illustrates an enlarged top perspective view of the apparatus with two straps, and indicating the manner in which one such strap may be positioned for receipt through a loop attached to the bottom portion of the support and thence connected to one end of the same strap.
Figure 9:
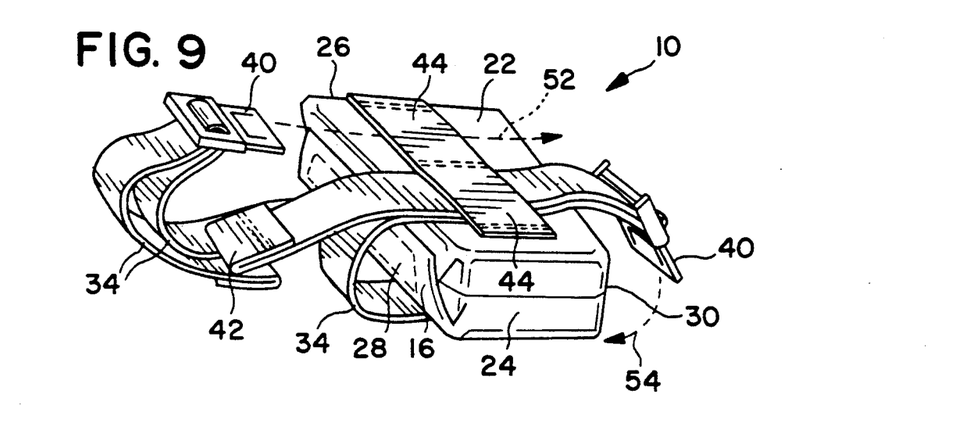
FIGS. 9 illustrates an enlarged bottom perspective view of the apparatus with two straps, and showing the manner in which one such strap has been positioned through a loop attached to the bottom portion of the support, and how a second strap is positioned for receipt through a second loop attached to the bottom portion of the support.

In FIG. 8 a perspective view of the apparatus 10 is shown looking downwardly toward the top portion 20 and front end 24 of the floatation support 12. In this view one of the straps 34 has been folded and positioned for insertion through a loop 44, as indicated be arrow 52, and thence to be wrapped around the distal side 30, as indicated by arrow 54. FIG. 9 illustrates a perspective view of the apparatus looking downwardly toward the bottom portion 22 and front end 24 of the floatation support 12. In this view one of the straps 34 has had the male portion 40 of the buckle 36 inserted through one of the loops 44 and in position for wrapping around the distal side 30 as indicated by arrow 54. The second strap 34 has also been folded and is now ready for the insertion of male portion 40 of the buckle 36 through the second loop 44 as indicated by arrow 52.

Figure 10:
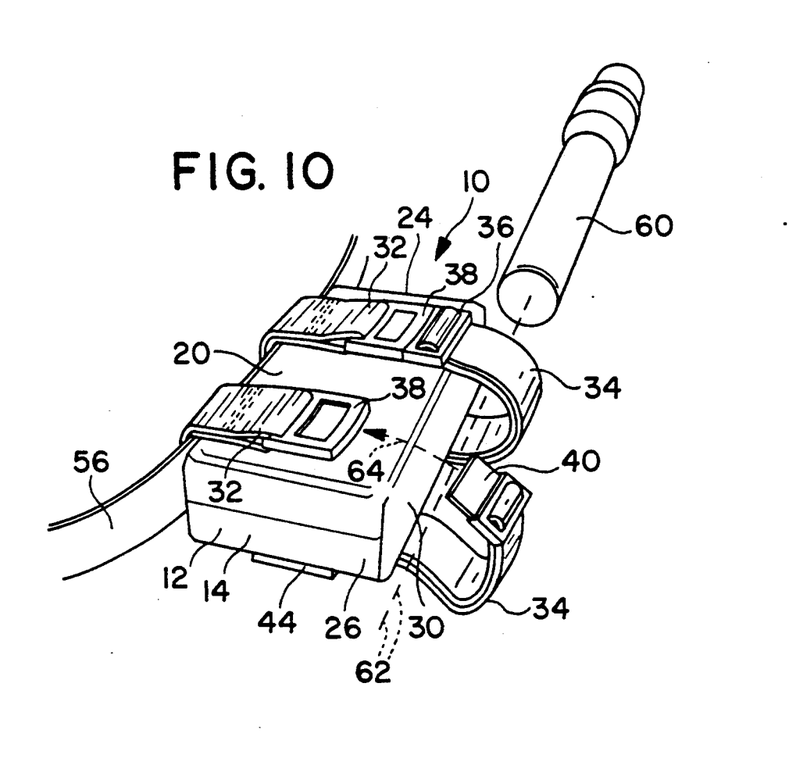
FIGS. 10-11 illustrate perspective views of the apparatus of the present invention attached to a portion of a strap of the mask of a diver and positioned, respectively for receipt of a flashlight and with a flashlight attached thereto.
Figure 11:
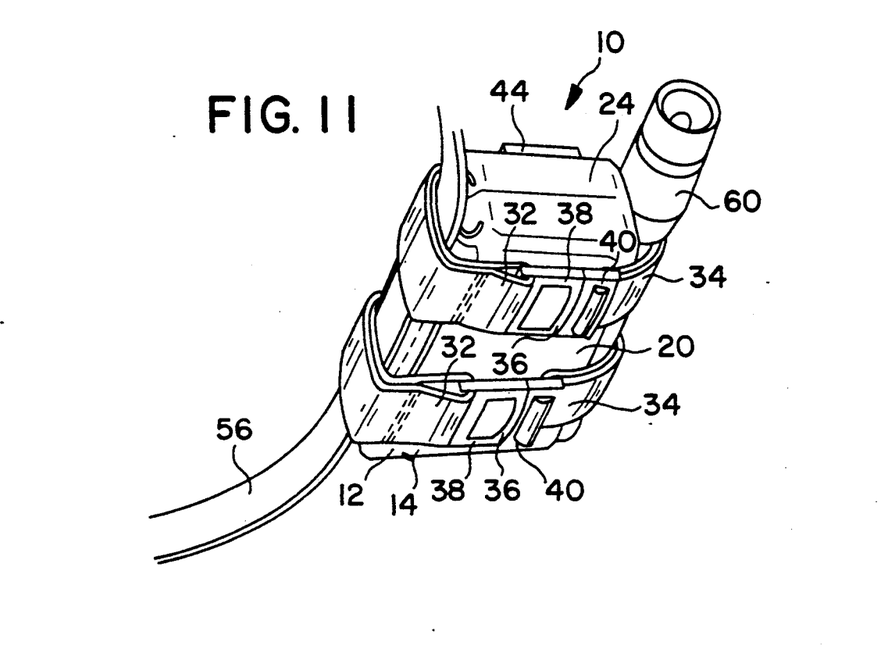

Now, referring to FIG. 10, the straps 34 of the apparatus 10 are shown wrapped around a portion of a dive mask strap 56. A dive mask 58 is shown in FIGS. 12–15. The dive mask strap 56 is secured against the proximal side 28 of the floatation support 12 by the straps 56 wrapped therearound. By holding the strap 56 against the proximal side 28, the flaps 16 (FIGS. 1, 3, 6, and 7–9) are further prevented from being unfolded. In the perspective view of FIG. 10, an underwater flashlight 60 is shown positioned for receipt next to the distal side 30 of the support 12 as indicated by the dashed line 62. One of the straps 34 in this figure has been connected using the buckle 36, while the other strap 34 has portion 40 of the buckle 36 in position for insertion, as indicated by arrow 64, into portion 38 disposed on the top portion 20 of the support 12. In FIG. 11 the flashlight 60 has been secured against the distal side 30 of the support 12 by the buckling of the two straps 34. Should the straps 34 need to be tightened on the support 12, the body of the straps 34 can be adjusted on the buckles 36. The apparatus 10 with flashlight 60, as shown in FIG. 11, is now ready for underwater use. FIG. 11 also serves to show a system in which flashlight 60 and support 12 are a single combined unit.

Figure 12:
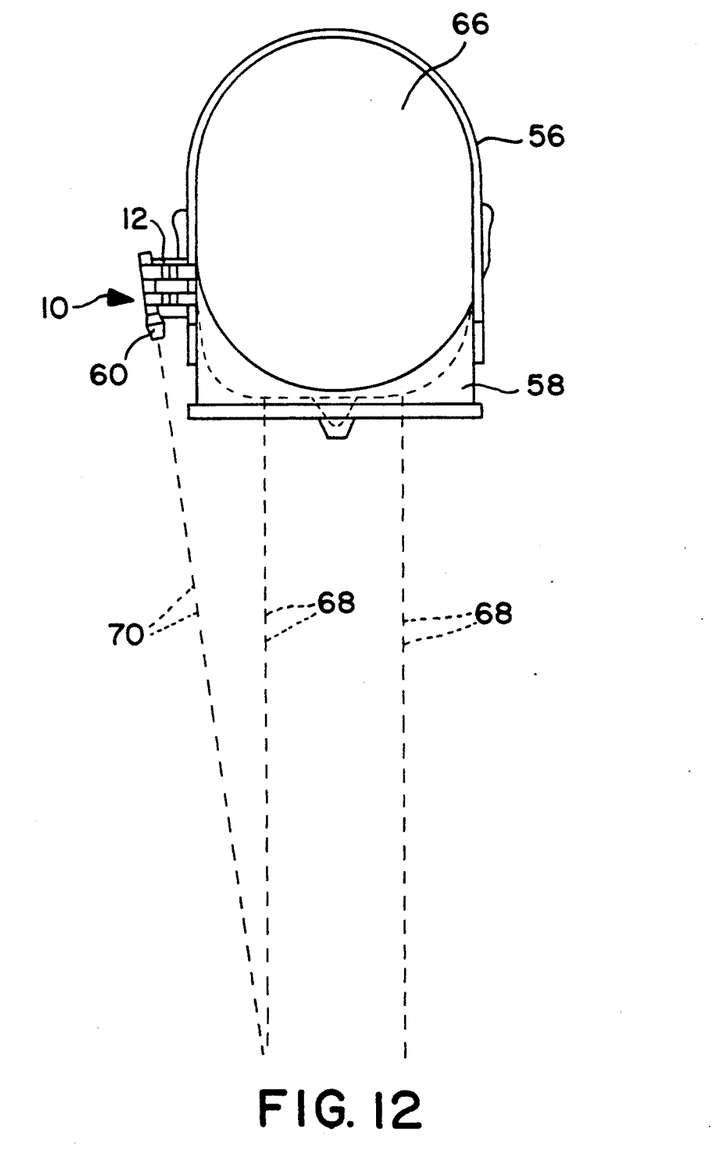
FIGS. 12-13 show a top plan view and a perspective view, respectively, of a the head of a diver wearing a mask, and illustrating a beam of light from a lit flashlight angled inwardly and merging with the short range line of sight of the diver.
Figure 13:
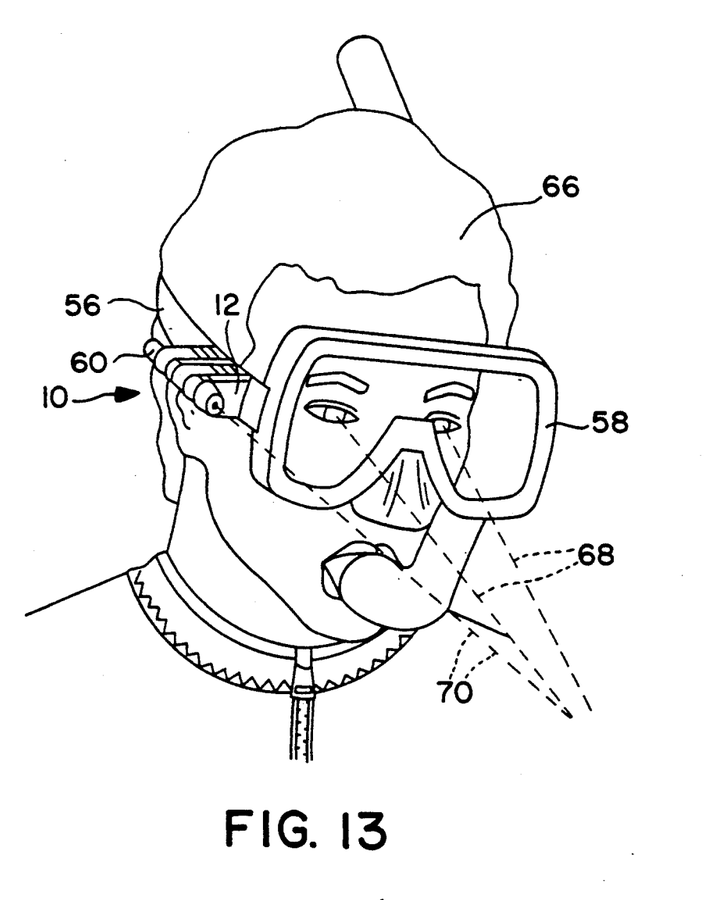

In FIGS. 12 and 13 a top view and a perspective view, respectively, of a head of a diver 66 are shown wearing a mask 58 secured by a mask strap 56. In these views the short range line of sight of the diver is shown as a pair of dotted lines 68. As mentioned above, the distal side 30 of the floatation support 12 is angled inwardly from the rear end 26 to the front end 24, which in turn directs a light beam, shown as a dotted line 70, inwardly toward the short range line of sight 68. While the light beam 70 can be directed inwardly at various angles, a preferred angle will place the light beam 70 merging with the line of sight 68 at about an arm's length in front of the head of the diver 66, or in a range of about two and one-half feet to about three and one-half feet. This distance will allow the light beam 70 to focus on anything being examined by the diver or held in the hand of the diver.

Figure 14:
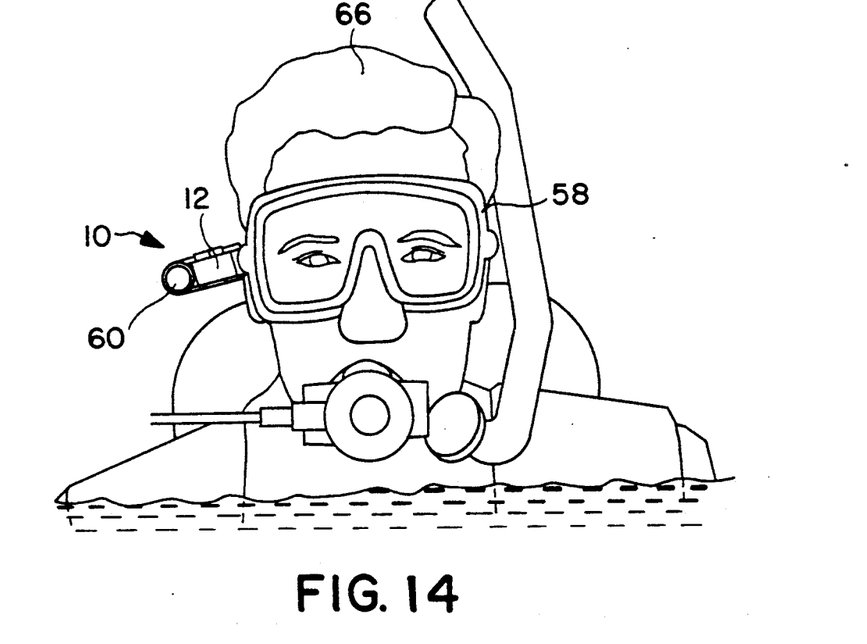
FIGS. 14-15 illustrate a front view of a diver wearing a mask, and with the subject invention attached to a portion the strap of the mask, with the head of the diver above water in FIG. 14 and the head of the diver submerged in FIG. 15, and illustrating the buoyancy of the apparatus of the present invention.
Figure 15:
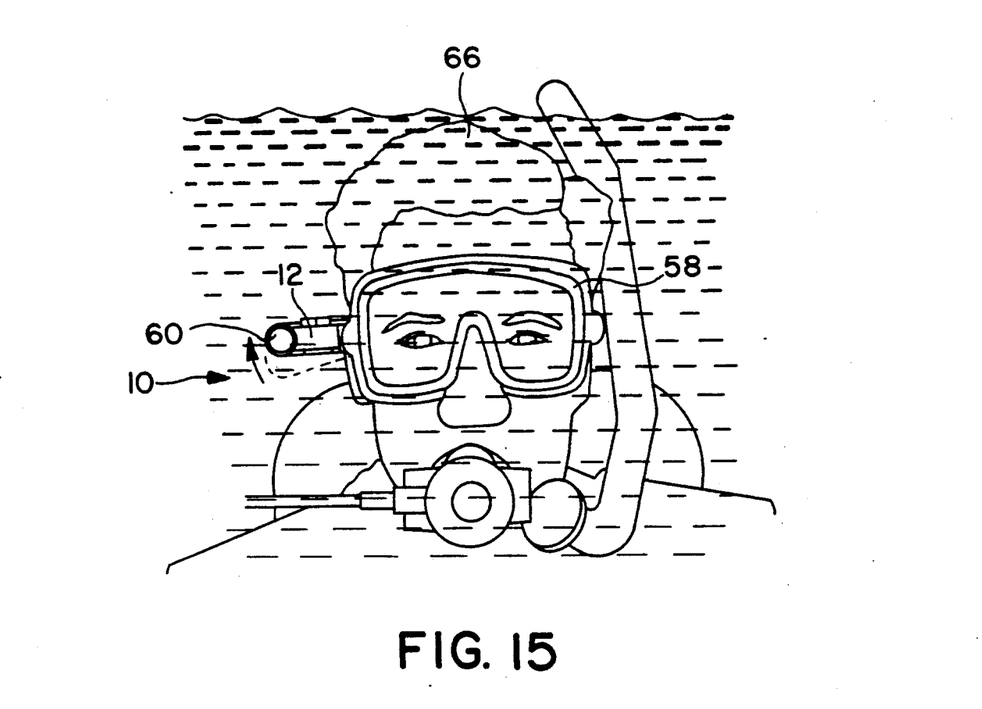

In FIGS. 14 and 15 the head of the diver 66 is shown first above a water surface 72 and then submerged below the surface 72. In FIG. 14 the apparatus 10 is shown attached to the dive mask strap 56 with the floatation support 12 and attached flashlight 60 drooping slightly from the horizontal. When the diver is underwater, as shown in FIG. 15, and because of the buoyancy of the floatation support 12, the apparatus 10 with flashlight 60 swings upwardly into a horizontal position and perpendicular to the side of the head of the diver 66.

It is therefore seen that the present invention provides a light weight, inexpensive, streamlined apparatus for holding a flashlight or other small object adjacent to the side of the head of an underwater diver, thereby freeing the hands of the diver for other purposes, while still providing underwater lighting or other equipment. In addition, it is seen that the present invention provides such an apparatus which is designed for releasable connection to head gear worn by underwater divers, and which includes an element for providing support orientation to a flashlight, including such a support element which has a specific gravity of less than about one, thereby providing floatation to the apparatus and to any article which is carried by the apparatus, as well as support to a flashlight or other equipment which is carried by the apparatus. In addition, the apparatus of the present invention provides a system for releasably connecting the apparatus of the present invention to the head gear of a diver and to a flashlight, and further includes a structure for orienting the light beam of a lit flashlight inwardly in the direction of the line of sight and close range visual focus of a diver when underwater, yet in which the flashlight is secured to the support at a distance away from the head of a diver in order to keep the flashlight from being deflected by any head hear worn by the diver. Furthermore, the present invention provides such an apparatus for holding a flashlight underwater, which is inexpensive, simple in design yet rugged in construction, colorful, and made of long lasting, durable materials.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed, except as precluded by the prior art.

The embodiments of the invention for which an exclusive privilege and property right is claimed are defined as follows:

1. An apparatus for holding a flashlight adjacent to the side of the head gear of a diver, said apparatus comprising:
   means for providing support and floatation to a flashlight, said flashlight support and floatation means having a proximal side adapted to be held adjacent to the head gear of a diver, and a distal side which is spaced from and opposed to said proximal side;
   means for releasably engaging and securing a flashlight to said flashlight support and floatation means; and
   means for releasably engaging and securing said flashlight support and floatation means to the head gear of a diver.

2. The apparatus as described in claim 1 wherein said flashlight support means has a specific gravity of less than one, whereby said flashlight support means is also capable of providing buoyancy to the apparatus as well as to a flashlight when said apparatus is underwater and carrying a flashlight.

3. The apparatus as described in claim 2 wherein said means for relesably engaging and securing a flashlight to said flashlight support means, and said means for releasably engaging and securing said flashlight support means to the head gear of a diver are the same combined means.

4. The apparatus as described in claim 3 wherein said combined means for releasably engaging and securing a flashlight to said flashlight support means and for releasably engaging and securing said flashlight support means to the head gear of a diver is one or more strap.

5. The apparatus as described in claim 4 wherein there is at least one strap, said strap including a first end portion, a second end portion, and a body portion intermediate said first end portion and said second end portion, said strap including means for adjustably and releasably attaching one portion of said strap to another portion of said strap, said strap being positioned to normally circumscribe said support means with one portion of said strap adjustably and releasably attached to another portion of said strap, said strap being adapted to be connected to the head gear of a diver in a manner such that said proximal side of said support means will be secured adjacent to the side of the head gear of a diver, said same strap being further adapted to secure a flashlight to said support means.

6. The apparatus as described in claim 5 wherein said strap is swingably connected to the head gear of a diver; whereby, when said apparatus is secured adjacent to the side of the head gear of a diver and is submerged in water the support means can swing upwardly to provide buoyancy to a flashlight carried by said apparatus.

7. The apparatus as described in claim 5 wherein a portion of said strap is secured to said support means.

8. The apparatus as described in claim 5 wherein said strap is adapted to secure a flashlight to said distal side of said support means, at a distance from the head gear of a diver.

9. The apparatus as described in claim 6 wherein said support means includes means for orienting the light beam of a lit flashlight carried by said apparatus inwardly in the direction of the close range line of sight of a diver when underwater and wearing head gear to which said apparatus has been attached with one or more strap.

10. The apparatus as described in claim 9 wherein said combined support and orientation means is a hexahedron having a top portion, a bottom portion, a front portion, and a rear portion in addition to a proximal side and a distal side, wherein, however, said distal side includes means for orienting a flashlight inwardly from the rear portion toward the front portion of said support and orientation means so that when said apparatus is secured adjacent to the side of the head gear of a diver worn by a diver and the diver submerges in water the combined support and orientation means will bring the beam of a lit flashlight carried by said apparatus into alignment with the short range line of sight of the diver.

11. The apparatus as described in claim 1 wherein said support means includes solid foam material.

12. The apparatus as described in claim 11 wherein said solid foam material has a specific gravity of less than about one.

13. The apparatus as described in claim 5 wherein fabric is attached to at least a portion of said support means.

14. The apparatus as described in claim 13 wherein said strap is connected to said fabric.

15. The apparatus as described in claim 13 wherein said fabric forms a package which substantially completely covers and encloses said support means.

16. An apparatus for holding a flashlight adjacent to the side of the head gear of a diver, said apparatus comprising:

means for providing support and orientation to a flashlight, said flashlight support and orientation means having a proximal side adapted to be located adjacent to the head gear of a diver who is wearing head gear, and a distal side which is spaced from and opposed to said proximal side, said flashlight support and orientation means including solid foam material having a specific gravity of less than about one, whereby said flashlight support and orientation means is also capable of providing buoyancy to the apparatus as well as support and orientation to a flashlight when underwater and carrying a flashlight;

combined means in the form of at least one strap for releasably engaging and securing a flashlight to said flashlight support and orientation means, and for releasably engaging and swingably securing said flashlight support and orientation means to the head gear of a diver, wherein said strap includes a first end portion, a second end portion, and a body portion intermediate said first end portion and said second end portion, said strap including means for adjustably and releasably attaching one portion of said strap to another portion of said strap, said strap being positioned to normally circumsribe said floatation support and orientation means, said strap being adapted to be connected to the head gear of a diver in a manner such that said proximal side of said floatation support and orientation means will be secured adjacent to the side of the head gear of a diver, said strap being further adapted to secure a flashlight to said distal side of said floatation support and orientation means, and spaced from the head gear of a diver.

17. The apparatus as described in claim 16 wherein said strap is swingably connected to the head gear of a diver, and wherein said distal side of said floatation support and orientation means includes means for orienting a flashlight; whereby, when said apparatus is secured adjacent to the side of the head gear of a diver worn by a diver and the diver submerges in water, the floatation support and orientation means will swing upwardly and be so inwardly oriented as to bring the light beam of a lit flashlight carried by said apparatus into alignment with the close range line of sight of a diver when underwater and wearing head gear to which said apparatus has been attached with one or more strap.

18. An appratus for holding a flashlight underwater and secured to a portion of underwater dive equipment, the apparatus comprising:

a flashlight for underwater use;

floatation support and orientation means for providing buoyancy to the apparatus when underwater and supporting said flashlight thereagainst; and at least one strap for releasably engaging said flashlight and securing said flashlight to said floatation support and orientation means and releasably engaging a portion of the dive equipment and holding the apparatus thereon.

19. The apparatus as described in claim 18 further including flashlight orienting means incorporated in said floatation support and orientation means and along one side thereof for directing the light beam of a lit flashlight toward fhe line of sight of a diver.

20. The apparatus as described in claim 18 wherein said floation support and orientation means and said flashlight are a single combined unit having a combined specific gravity of less than about one.

* * * * *